(12) United States Patent
Roth et al.

(10) Patent No.: US 7,989,474 B2
(45) Date of Patent: Aug. 2, 2011

(54) USE OF LCK INHIBITORS FOR TREATMENT OF IMMUNOLOGIC DISEASES

(75) Inventors: Gerald Juergen Roth, Biberach (DE); Armin Heckel, Biberach (DE); Rainer Walter, Biberach (DE); Frank Hilberg, Vienna (AT); Rudolf Hauptmann, Ebreichsdorf (AT); Martin Fredrich Stefanic, Warthausen-Birkenhard (DE); Florian Colbatzky, Stafflangen (DE); Steffan Ernest, Moelnlycke (SE)

(73) Assignee: Boehringer Ingelheim Pharma GmbH & Co. KG, Ingelheim am Rhein (DE)

( * ) Notice: Subject to any disclaimer, the term of this patent is extended or adjusted under 35 U.S.C. 154(b) by 236 days.

(21) Appl. No.: 12/334,323

(22) Filed: Dec. 12, 2008

(65) Prior Publication Data

US 2009/0087405 A1    Apr. 2, 2009

Related U.S. Application Data

(62) Division of application No. 10/640,926, filed on Aug. 14, 2003, now abandoned.

(60) Provisional application No. 60/409,204, filed on Sep. 9, 2002.

(30) Foreign Application Priority Data

Aug. 16, 2002    (DE) .................................. 102 37 423

(51) Int. Cl.
    *A61K 31/445*    (2006.01)

(52) U.S. Cl. ........................................................ 514/323

(58) Field of Classification Search .................. None
    See application file for complete search history.

(56) References Cited

U.S. PATENT DOCUMENTS

| 5,922,741 | A | 7/1999 | Davis et al. |
|---|---|---|---|
| 6,093,716 | A | 7/2000 | Davis et al. |
| 6,169,106 | B1 | 1/2001 | Heckel et al. |
| 6,245,760 | B1 | 6/2001 | He et al. |
| 6,762,180 | B1* | 7/2004 | Roth et al. ............ 514/228.2 |
| 6,794,395 | B1 | 9/2004 | Roth et al. |
| 7,119,093 | B2 | 10/2006 | Roth et al. |
| 7,148,249 | B2 | 12/2006 | Kley et al. |
| 7,160,901 | B2 | 1/2007 | Walter et al. |
| 2003/0069299 | A1 | 4/2003 | Walter et al. |
| 2003/0166929 | A1 | 9/2003 | Snow et al. |

FOREIGN PATENT DOCUMENTS

| WO | 0018734 A | 4/2000 |
|---|---|---|
| WO | 0073297 A | 12/2000 |
| WO | 0127080 A | 4/2001 |
| WO | 0127081 A | 4/2001 |
| WO | WO - 0127081 * | 4/2001 |
| WO | 0140215 A | 6/2001 |
| WO | 0172711 A | 10/2001 |

OTHER PUBLICATIONS

U.S. Appl. No. 11/275,223.

* cited by examiner

*Primary Examiner* — Alton Pryor

(74) *Attorney, Agent, or Firm* — Michael P. Morris; Alan R. Stempel

(57) ABSTRACT

The invention relates to a method of treating immunologic diseases or pathological conditions involving an immunologic component using certain Lck inhibitors already known as kinase inhibitors for therapy in oncology, optionally in combination with one or more other drugs selected from NSAIDs, steroids, DMARDs, immunsuppressives, biologic response modifiers and antinfectives, pharmaceutical compositions comprising said Lck inhibitors together with said other drugs, and the use of the Lck inhibitors for the manufacture of a pharmaceutical composition for the treatment of immunologic diseases or pathological conditions involving an immunologic component.

2 Claims, No Drawings

USE OF LCK INHIBITORS FOR TREATMENT OF IMMUNOLOGIC DISEASES

CROSS-REFERENCE TO RELATED APPLICATIONS

This application is a divisional application and claims the benefit of U.S. patent application Ser. No. 10/640,926, filed Aug. 14, 2003, and U.S. Provisional Patent application 60/409,204, filed Sep. 9, 2002 the entireties of which are incorporated by reference herein.

TECHNICAL FIELD OF THE INVENTION

This invention relates to a method for treating immunologic diseases or pathological conditions, which conditions have an immunologic component, using a compound selected from compounds (A) to (AL) listed below. Such compounds are already known as kinase inhibitors for therapy in oncology.

BACKGROUND OF THE INVENTION

Compounds (A) to (AL) listed below, their preparation as well as the pharmacological activity of these compounds based on inhibition of kinases, e.g., VEGFR-2, suitable for therapy in oncology, are disclosed in WO 02/36564, WO 99/52869, WO 00/18734, WO 00/73297, WO 01/27080, WO 01/27081 and WO 01/32651. The cited documents are herewith incorporated by reference.

Lck, a further tyrosine kinase belonging to the src family of tyrosine kinases not mentioned in the references cited above, is functionally required for T-cell activation through the T-cell antigen receptor (TCR) (see A. E. Nel: T-cell activation through antigen receptor. Part 1: Signaling components, signaling pathways, and signal integration at the T-cell antigen receptor synapse. *J. Allergy Clin Immunol*, 109, 5, 758-770, 2002) and possibly T-cell survival (Seddon, B.; Legname, G.; Tomlinson, P.; Zamoyska, R.: Long-term survival but impaired homeostatic proliferation of naive T cells in the absence of p56(lck). *Science* 290: 127-131, 2000). Therefore, any Lck inhibitor has a high possible therapeutic potential in the treatment of T-cell mediated diseases, e.g., in the treatment of immunologic diseases. Certain autoimmune diseases such as inflammatory diseases (for example, inflammatory bowel disease, rheumatoid arthritis, glomerulonephritis and lung fibrosis, psoriasis, hypersensitivity reactions of the skin, atherosclerosis, restenosis, allergic asthma, multiple sclerosis and type 1 diabetes) are believed to be associated with inappropriate T cell activation (J. H. Hanke et al., Inflamm. Res., 1995, 357). In addition, the acute rejection of transplanted organs as well as Graft versus Host Disease (GvHD) after allogeneic bone marrow and stem cell transplantation can also be interpreted as a consequence of inappropriate T cell activation. Lck inhibitors offer an approach for treatment of the indications mentioned hereinbefore. Agents of this kind would offer therapy for transplant rejection and autoimmune diseases whilst avoiding toxicities associated with the commonly used, less selective immunosuppressants. The leading agent for prevention or treatment of transplant rejection is cyclosporin A which, although effective, is often associated with side-effects such as renal damage and hypertension, which results in kidney failure in a substantial number of patients. It is contemporary practice to treat rheumatoid arthritis initially with symptom relief agents such as NSAIDs, which have no effect on disease progression and are often associated with unwanted side-effects. A rationally based, disease modifying agent, without such deleterious side-effects, would therefore offer significant benefits in the prevention or treatment of transplant rejection or autoimmune conditions such as rheumatoid arthritis.

There is considerable evidence that VEGF plays a key role in the pathogegenesis in rheumatoid arthritis, especially in the formation of the pannus (Paleolog E M, Arthritis Res 2002; 4 Suppl 3:S81-90, Pavonen et al, J Rheumatol 2002 January; 29(1):39-45, Afuwape A O et al, Histol Histopathol 2002; 17(3):961-72). Thus, combined inhibition of VEGFR-tyrosine kinases and Lck is considered of potentially high benefit for patients with this disease. The same considerations can be applied to psoriasis and inflammatory bowel disease (Folkman J, Nat. Med. 1995 January; 1(1):27-31. Review; Griga T et al, Hepatogastroenterology 2002 January-February; 49(43): 116-23, Creamer D et al, Arch Dermatol 2002 June; 138(6):791-6).

BRIEF SUMMARY OF THE INVENTION

In view of the work cited above, there is a clear need for compounds which are Lck inhibitors for the treatment of T-cell mediated diseases, e.g., in the treatment of immunologic diseases or pathological conditions involving an immunologic component.

It is therefore an object of the invention to provide a method for treating immunologic diseases, or pathological conditions involving an immunologic component, comprising administering to a patient in need of such treatment an effective amount of a pharmaceutical composition comprising a compound selected from compounds (A) to (AL), which compounds are already known as agents usefully in oncology.

A second object of the invention is a pharmaceutical composition comprising a compound selected from compounds (A) to (AL) together with one or more other drugs selected from nonsteroidal anti-inflammatory drugs (NSAIDs), steroids, disease-modifying antirheumatic drugs (DMARDs), immunsuppressives, biologic response modifiers and antinfectives for use in treatment of immunologic diseases or pathological conditions involving an immunologic component.

A third object of the invention is the use of a compound selected from compounds (A) to (AL) for the manufacture of a pharmaceutical composition for the treatment of immunologic diseases or pathological conditions involving an immunologic component.

DETAILED DESCRIPTION OF THE INVENTION

It has now surprisingly been found that compounds
(A) (Z)-3-(1-(4-(piperidin-1-yl-methyl)-phenylamino)-1-phenyl-methylene)-5-(methylsulfonylamino)-2-indolinone;
(B) (Z)-3-(1-(4-(piperidin-1-yl-methyl)-phenylamino)-1-phenyl-methylene)-5-(ethylsulfonylamino)-2-indolinone;
(C) (Z)-3-(1-(4-(dimethylaminomethyl)-phenylamino)-1-phenyl-methylene)-5-(ethylsulfonylamino)-2-indolinone;
(D) (Z)-3-(1-(4-(piperidin-1-yl-methyl)-phenylamino)-1-phenyl-methylene)-5-(phenylsulfonylamino)-2-indolinone;
(E) (Z)-3-(1-(4-(piperidin-1-yl-methyl)-phenylamino)-1-phenyl-methylene)-5-(4-amino-phenylsulfonylamino)-2-indolinone;
(F) (Z)-3-(1-(4-(pyrrolidin-1-yl-methyl)-phenylamino)-1-phenyl-methylene)-5-(ethylsulfonylamino)-2-indolinone;

(G) (Z)-3-(1-(4-(4-(3-aminopropyl-piperidin-1-yl-methyl)-phenylamino)-1-phenyl-methylene)-5-(ethylsulfonylamino)-2-indolinone;

(H) (Z)-3-(1-(4-(N-(piperidin-1-yl-methylcarbonyl)-N-methyl-amino)-phenylamino)-1-phenyl-methylene)-5-(phenylsulfonylamino)-2-indolinone;

(I) (Z)-3-(1-(4-(N-(2-dimethylamino-ethyl)-N-methylsulfonyl-amino)-phenylamino)-1-phenyl-methylene)-5-(N-methyl-N-phenylsulfonyl-amino)-2-indolinone;

(J) (Z)-3-(1-(4-(N-methyl-N-(piperidin-1-yl-methylcarbonyl)-amino)-phenylamino)-1-phenyl-methylene)-5-(N-methyl-N-phenylsulfonyl-amino)-2-indolinone;

(K) (Z)-3-(1-(2-benzimidazolyl-amino)-1-phenyl-methylene)-5-amido-2-indolinone;

(L) (Z)-3-(1-(4-(N-methyl-propionylamino)-phenylamino)-1-phenyl-methylene)-5-amido-2-indolinone;

(M) (Z)-3-(1-(4-(N-(2-dimethylamino-ethyl)-N-methylsulfonyl-amino)-phenylamino)-1-phenyl-methylene)-2-indolinone;

(N) (Z)-3-(1-(4-(N-(3-dimethylaminopropyl)-N-propionyl-amino)-phenylamino)-1-phenyl-methylene)-2-indolinone;

(O) (Z)-3-(1-(4-(dimethylaminomethyl)-phenylamino)-1-phenyl-methylene)-5-(butylcarbamoyl)-2-indolinone;

(P) (Z)-3-(1-(4-(dimethylaminomethyl)-phenylamino)-1-phenyl-methylen)-5-(naphth-1-yl-methyl-carbamoyl)-2-indolinone;

(Q) (Z)-3-(1-(4-(dimethylaminomethyl)-phenylamino)-1-phenyl-methylene)-5-(N-butyl-N-phenyl-carbamoyl)-2-indolinone;

(R) (Z)-3-(1-(4-(dimethylaminomethyl)-phenylamino)-1-phenyl-methylen)-5-(hexylcarbamoyl)-2-indolinone;

(S) (Z)-3-(1-(4-(dimethylaminomethyl)-phenylamino)-1-phenyl-methylen)-5-(cyclohexylmethyl-carbamoyl)-2-indolinone;

(T) (Z)-3-(1-(4-(N-methylsulfonyl-N-(2-dimethylamino-ethyl)-amino)-phenylamino)-1-phenyl-methylen)-5-(cyclohexylmethyl-carbamoyl)-2-indolinone;

(U) (Z)-3-(1-(4-(butylaminomethyl)-phenylamino)-1-phenyl-methylen)-5-(cyclohexylmethyl-carbamoyl)-2-indolinone;

(V) (Z)-3-(1-(4-(pyrrolidin-1-yl-methyl)-phenylamino)-1-phenyl-methylen)-5-(cyclohexylmethyl-carbamoyl)-2-indolinone;

(W) (Z)-3-(1-(4-(diethylaminomethyl)-phenylamino)-1-phenyl-methylen)-5-(cyclohexylmethyl-carbamoyl)-2-indolinone;

(X) (Z)-3-(1-(4-(diethylaminomethyl)-phenylamino)-1-phenyl-methylen)-5-(N-(3-chlorobenzyl)-carbamoyl)-2-indolinone;

(Y) (Z)-3-(1-(4-(diethanolaminomethyl)-phenylamino)-1-phenyl-methylen)-5-(butylcarbamoyl)-2-indolinone;

(Z) (Z)-3-(1-(4-(dimethylaminomethyl)-phenylamino)-1-phenyl-methylen)-5-(N-(3-chlorobenzyl)-carbamoyl)-2-indolinone;

(AA) (Z)-3-(1-(4-(N-acetyl-N-(2-dimethylamino-ethyl)-amino)-phenylamino)-1-phenyl-methylen)-5-(N-(3-chlorobenzyl)-carbamoyl)-2-indolinone;

(AB) (Z)-3-(1-(4-(butylaminomethyl)-phenylamino)-1-phenyl-methylen)-5-(N-(3-chlorobenzyl)-carbamoyl)-2-indolinone;

(AC) (Z)-3-(1-(4-(piperidin-1-yl-methyl)-phenylamino)-1-phenyl-methylene)-5-(N-methyl-N-phenyl-aminosulfonyl)-2-indolinone;

(AD) (Z)-3-(1-(4-(piperidin-1-yl-methyl)-phenylamino)-1-phenyl-methylene)-5-(N-butyl-N-methyl-aminosulfonyl)-2-indolinone (AE) (Z)-3-(1-(4-(dimethylaminomethyl)-phenylamino)-1-phenyl-methylene)-6-methoxycarbonyl-2-indolinone;

(AF) (Z)-3-(1-(4-(N-(3-dimethylamino-propyl)-N-acetyl-amino)-phenylamino)-1-phenyl-methylene)-6-methoxycarbonyl-2-indolinone;

(AG) (Z)-3-(1-(4-(ethylaminomethyl)-phenylamino)-1-phenyl-methylene)-6-methoxycarbonyl-2-indolinone;

(AH) (Z)-3-(1-(4-(1-methyl-imidazol-2-yl)-phenylamino)-1-phenyl-methylene)-6-methoxycarbonyl-2-indolinone;

(AI) (Z)-3-(1-(4-(N-(dimethylaminomethylcarbonyl)-N-methyl-amino)-phenylamino)-1-phenyl-methylene)-6-methoxycarbonyl-2-indolinone;

(AJ) (Z)-3-(1-(4-(methylaminomethyl)-anilino)-1-phenyl-methylene)-6-methoxycarbonyl-2-indolinone;

(AK) (Z)-3-(1-(4-(N-((4-methyl-piperazin-1-yl)-methylcarbonyl)-N-methyl-amino)-phenylamino)-1-phenyl-methylene)-6-methoxycarbonyl-2-indolinone; and (AL) 4-(4-bromo-2-fluoroanilino)-6-methoxy-7-(1-methylpiperidin-4-ylmethoxy)-quinazoline, the tautomers, the stereoisomers and the physiologically acceptable salts thereof, are effective inhibitors of Lck and therefore are especially suitable and effective in the treatment of immunologic diseases or pathological conditions involving an immunologic component.

Compounds (A) to (J) are described in WO 02/36564, compounds (K) to (L) are described in WO 99/52869, compounds (M) to (N) are described in WO 00/18734, compounds (O) to (AB) are described in WO 00/73297, compounds (AC) to (AD) are described in WO 01/27080, compounds (AE) to (AK) are described in WO 01/27081, and compound (AL) is described in WO 01/32651.

Viewed from a first aspect, the present invention provides a method for treating immunologic diseases or pathological conditions involving an immunologic component comprising administering to a patient in need of such treatment an effective amount of a pharmaceutical composition comprising a compound selected from compounds (A) to (AL), the tautomers, the stereoisomers and the physiologically acceptable salts thereof, optionally in combination with one or more other drugs selected from NSAIDs, steroids, DMARDs, immunsuppressives, biologic response modifiers and antinfectives.

The expression "patient" is meant to comprise the human and the non-human mammal patient.

The indication "immunologic diseases or pathological conditions involving an immunologic component" should be understood in a non-limiting manner to comprise:

autoimmune diseases, for instance inflammatory diseases having an autoimmune component such as inflammatory diseases selected from
  inflammatory bowel disease (e.g., colitis ulcerosa and Morbus Crohn), rheumatoid arthritis, glomerulonephritis and lung fibrosis,
furthermore, psoriasis, psoriasis arthritis, hypersensitivity reactions of the skin, atherosclerosis, restenosis, asthma, multiple sclerosis and type 1 diabetes,
and indications which need immunosuppressant therapy, for instance prevention or therapy of tissue or organ transplant rejection, e.g., acute or chronic graft-versus-host disease, allograft or xenograft rejection etc. (the transplanted organ being kidney, heart, liver, lung, bone marrow, peripheral blood stem cells, pancreas or islet cells thereof, cornea, small bowel, skin, or heart valve).

Preferred indications which may be treated by the method according to the invention are
  rheumatoid arthritis,
  inflammatory bowel disease such as colitis ulcerosa and Morbus Crohn, psoriasis, psoriasis arthritis, prevention or therapy of tissue or organ transplant rejection, acute or chronic graft-versus-host disease, allograft or xenograft rejection, and allergic asthma, multiple sclerosis and type 1 diabetes.

A further subgroup of indications which may be treated by the method according to the invention, and deserves special mention, comprises morbus crohn, lung fibrosis, psoriasis arthritis, hypersensitivity reactions of the skin, graft-versus-host disease (acute and chronic), asthma, multiple sclerosis and type 1 diabetes.

A preferred embodiment of the method according to the invention comprises administration of a compound selected from compounds (A), (B), (C), (D), (F), (G), (P), (T), (V), (X), (Z), (AA), (AE), (AI), (AK) and (AL), the tautomers, the stereoisomers and the physiologically acceptable salts thereof, optionally in combination with one or more other drugs selected from NSAIDs, steroids, DMARDs, immunsuppressives, biologic response modifiers and antinfectives.

Another preferred embodiment of the method according to the invention comprises administration of a compound selected from the following combined inhibitors of VEGFR-2 and Lck:

(M), (N), (O), (S), (T), (U), (V), (W), (X), (Y), (Z), (AA), (AB), (AE), (AF), (AG), (AH), (AI), (AJ), (AK) and (AL), the tautomers, the stereoisomers and the physiologically acceptable salts thereof, optionally in combination with one or more other drugs selected from NSAIDs, steroids, DMARDs, immunsuppressives, biologic response modifiers and antinfectives. Since VEGF also plays an important pathogenetical role in chronic inflammatory bowel diseases such as colitis ulcerosa and morbus crohn as well as in rheumatoid arthritis, psoriasis and psoriasis arthritis, these combined inhibitors of VEGFR-2 and Lck are of special advantage in these most preferred indications.

A further preferred embodiment of the method according to the invention comprises administration of a compound selected from compounds (AK), (AI) and (AL), the tautomers, the stereoisomers and the physiologically acceptable salts thereof, Especially preferred is administration of compound (AK).

In the method of treatment according to the invention compounds (A) to (AL) can be administered orally, parenterally, rectally or, with respect to indications involving treatment of the skin (such as psoriasis, psoriasis arthritis or hypersensitivity reactions of the skin), also in topical formulations. Oral administration is preferred.

In oral, rectal or topical administration, the compounds may be given, if required, in divided doses, in a daily dosage of 0.1 to 20 mg/kg body weight, preferably 0.5 to 20 mg/kg body weight, most preferred 1 to 10 mg/kg body weight.

Parenterally, the compounds may be administered in lower doses, for instance in a total daily dosage of 0.01 to 5 mg/kg body weight, preferably 0.05 to 2 mg/kg body weight, most preferred 0.1 to 1 mg/kg body weight.

For administration, the compounds may be formulated with one or more conventional inert carriers and/or diluents as known in the art, e.g., with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fatty substances such as hard fat or suitable mixtures thereof, in conventional galenic preparations such as plain or coated tablets, lozenges, hard or soft capsules, dispersible powders or granules, syrups or elixirs, injectable solutions, ampoules, aqueous or oily suspensions, emulsions, solutions, sprays, creams, ointments, gels, or suppositories. Suitable galenic formulations are disclosed in the documents cited hereinbefore.

Furthermore, in the method according to the invention a compound selected from compounds (A) to (AL) may be administered in combination, simultaneously or sequentially, with one or more other drugs selected from NSAIDs, steroids, DMARDs, immunsuppressives, biologic response modifiers, antinfectives and, in case of lung indications, also with bronchodilators.

In particular, a compound selected from compounds (A) to (AL) could be used in combination with immunosuppressives in the prevention or treatment of the acute rejection of transplanted organs, in combination with NSAIDs, steroids, immuno-supressives, DMARDs, biologic response modifiers (e.g., anti-TNF), and anti-infectives for the treatment of inflammatory bowel disease (e.g., colitis ulcerosa and morbus crohn), rheumatoid arthritis and psoriasis, whereby the NSAID-dose can be significantly reduced compared to what otherwise would be required or needed to produce a therapeutic effect. Thus, there would be a reduction in the risk of adverse side-effects from the NSAID, such as gastrointestinal effects.

Such compound selected from (A) to (AL) can also be used in combination with biologic response modifiers (e.g., leukotriene antagonists), and bronchodilators for the treatment of asthma.

Suitable NSAIDs for combination treatment are meant to include all COX (cyclooxygenase) inhibitors, e.g., non-selective COX-inhibitors such as acetylsalicyclic acid, mesalazin, ibuprofen, naproxen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen, indomethacin, sulindac, tolmetin, zomepirac, nabumetone, diclofenac, fenclofenac, alclofenac, bromfenac, ibufenac, aceclofenac, acemetacin, fentiazac, clidanac, etodolac, oxpinac, mefenamic acid, meclofenamic acid, flufenamic acid, niflumic acid, tolfenamic acid, diflunisal, flufenisal, piroxicam, tenoxicam, lornoxicam and nimesulide and the pharmaceutically acceptable salts thereof, as well as selective COX 2-inhibitors such as meloxicam, celecoxib and rofecoxib and the pharmaceutically acceptable salts thereof.

Suitable steroids for combination treatment are meant to include in a non-limiting manner prednisone, prednisolone, methylprednisolone, dexamethasone, budenoside, fluocortolone and triamcinolone.

Suitable DMARDs for combination treatment are meant to include in a non-limiting manner sulfasalazine, olsalazine, chloroquin, gold derivatives (Auranofin), D-penicillamine and cytostatics such as methotrexate and cyclophosphamide.

Suitable immunsuppressives for combination treatment are meant to include in a non-limiting manner cyclosporin A and derivatives thereof, mycophenolatemofetil, FK 506, OKT-3, ATG, 15-desoxyspergualin, mizoribine, misoprostol, rapamycin, reflunomide, azathioprine and NF-Kappa B-inhibitors.

Suitable biologic response modifiers for combination treatment are meant to include in a non-limiting manner interferon beta, anti-TNF-alpha (Etanercept), IL-10, oral and parenteral tolerance induction strategies (orally e.g., with genetically modified enteric bacteria), leukotrien-antagonists, anti-CD3 or anti-CD25.

Suitable antinfectives for combination treatment are meant to include in a non-limiting manner metronidazol and chinolone for treatment of chronic inflammatory bowel diseases.

Suitable bronchodilators for combination treatment are meant to include in a non-limiting manner those disclosed under "broncholytics/antiasthmatics" in Rote Liste® 2002, Editio Cantor Verlag Aulendorf, Germany, being herewith incorporated by reference, for instance ipratropium bromide, oxitropium bromide, tiotropium bromide, epinephrine hydrochloride, salbutamole, terbutaline sulfate, fenoterol hydrobromide, salmeterol, formoterol, cromiclinic acid, theophylline derivatives etc.

In such combinations each active ingredient can be administered either in accordance with its usual dosage range or a dose below its usual dosage range. The dosage for the combined NSAIDs, steroids, DMARDs, immunsuppressives, biologic response modifiers and antinfectives is appropriately 1/50 of the lowest dose normally recommended up to 1/1 of the normally recommended dosage, preferably 1/20 to 1/2 and more preferably 1/10 to 1/5. The normally recommended dose for the combined drug should be understood to be the dose disclosed for example in Rote Liste® 2002, Editio Cantor Verlag Aulendorf, Germany, or in Physician's Desk Reference.

It can be expected that combination treatment comprising administration of Lck inhibitors together with a second drug selected from those mentioned hereinbefore may provide synergistic efficacy, thus providing significant dose reduction compared to what would normally be required or necessary to produce a therapeutic effect. This would be especially beneficial with regard to medications having a high risk of adverse side-effects, as is the case with non-selective COX inhibitors, cyclosporin A or DMARDs.

Viewed from a second aspect, the present invention also relates to pharmaceutical compositions comprising
(a) a compound selected from compounds (A) to (AL), the tautomers, the stereoisomers and the physiologically acceptable salts thereof,
(b) and one or more other drugs selected from NSAIDs, steroids, DMARDs, immunsuppressives, biologic response modifiers and antinfectives, optionally together with pharmaceutically acceptable diluents and/or carriers, as a combined preparation or a kit of parts containing components (a) and (b) in separate containments for simultaneous, separate or sequential use in treatment of immunologic diseases or pathological conditions involving an immunologic component.

Viewed from a third aspect, the present invention provides the use of a compound selected from compounds (A) to (AL), the tautomers, the stereoisomers and the physiologically acceptable salts thereof, optionally in combination with one or more other drugs selected from NSAIDs, steroids, DMARDs, immunsuppressives, biologic response modifiers and antinfectives, for the manufacture of a pharmaceutical composition for the treatment of a patient suffering from immunologic diseases or pathological conditions involving an immunologic component.

Preferred embodiments of either the composition aspect or the use aspect of the invention with respect to the combined VEGFR-2/Lck component correspond to those mentioned hereinbefore for the method of treatment aspect.

EXAMPLE 1

Non-Radioactive Kinase Assay (lck)

Methodology

The lck enzyme comprises the entire lck molecule except the first nine amino acids which are replaced by an His-tag for purification purposes. The enzyme is affinity purified.

The assay mix is assembled in a well of a 96-well round bottom microtiter plate and contains 10 µl PBS (either as such or with an inhibitor dissolved at an appropriate concentration), 20 µl substrate solution (200 mM Hepes, pH=7.4; 50 mM MgAc$_2$; 1 mM Na$_3$VO$_4$; 250 µg/ml poly-Glu-Tyr (Sigma P0275); 200 ng/ml biotinylated peptide (biot-Ala-Glu-Glu-Glu-Ile-Tyr-Gly-Glu-Phe-Glu-Ala-Lys-Lys-Lys-Lys) and 20 µl of 2.5 ng/µl enzyme (diluted from affinity purified stock with enzyme dilution buffer, EDB: 20 mM Hepes, pH=7.4, 130 mM NaCl, 0.05% Triton X-100).

The reaction is started by the addition of 50 µl 500 µM ATP (in 10 mM MgAc$_2$) and is performed at room temperature. After 30 minutes 50 µl stop solution (20 mM Hepes, pH=7.4; 250 mM EDTA) are added and 100 µl of this solution transferred to the well of a streptavidin coated microtiter plate (SA-MTP, Boehringer Mannheim, #1664-760).

The solution is incubated for one hour at room temperature and the supernatant discarded. The well is washed twice with 300 µl PBS.

The streptavidin bound biotinylated peptide is incubated for 1 hour at room temperature with 100 µl Eu$^{3+}$-labelled anti-phosphotyrosine antibody solution (0.3 mg/ml DELFIA-Eu-labelled PT66 (Wallac, AD0041); 50 mM Tris, pH=7.8; 0.05% Tween 20; 0.5% (w7v) BSA (Serva, diagnostic grade) under gentle agitation. The well is washed three times with 1× Delfia wash buffer (Wallac, 1244-114, 25× concentrate, diluted with water) and finally 100 µl Delfia enhancement solution (Wallac, 1244-105) are added.

Time resolved fluorescence is measured in a Wallac Victor2 1420 Multilabel Counter, excitation is at 340 nm, emission is measured at 615 nm (delay time 400 µsec, window time 1000 µsec).

Results

In two independent experiments the IC$_{50}$s of compounds (A) to (AL) on the kinase have been determined. The data (mean values) obtained with three representative compounds are summarised in the following table:

| compound | Lck; IC$_{50}$ [nM] |
|---|---|
| (AK) | 16 |
| (AI) | 36 |
| (AL) | 58 |

Compounds (A) to (AH) and (AJ) inhibit the lck kinase function with an IC$_{50}$<1 µM.

What is claimed is:
1. A method for treating lung fibrosis comprising administering to a patient in need of such treatment an effective amount of a pharmaceutical composition comprising
(Z)-3-(1-(4-(N-((4-methyl-piperazin-1-yl)-methylcarbonyl)-N-methyl-amino)-phenylamino)-1-phenyl-methylene)-6-methoxycarbonyl-2-indolinone or a tautomer, stereoisomer or physiologically acceptable salt thereof.
2. The method according to claim 1, wherein the pharmaceutical composition is administered orally, parenterally, or rectally.

* * * * *